United States Patent [19]

Stanker et al.

[11] Patent Number: 5,466,784

[45] Date of Patent: Nov. 14, 1995

[54] MONOCLONAL ANTIBODIES TO SALINOMYCIN AND METHOD FOR DETECTING THE SAME

[75] Inventors: Larry H. Stanker; Marcel H. Elissalde, Jr.; Ross C. Beier, all of College Station; Loyd D. Rowe, Jr., Bryan; John R. DeLoach, College Station, all of Tex.

[73] Assignee: The United States of America as represented by the Secretary of Agriculture, Washington, D.C.

[21] Appl. No.: 81,591

[22] Filed: Jun. 23, 1993

[51] Int. Cl.⁶ .............................. C07K 16/00; C12N 5/18
[52] U.S. Cl. .................. 530/388.9; 530/808; 530/809; 435/7.92; 435/240.27; 435/810; 435/975
[58] Field of Search .......................... 435/7.92, 240.27, 435/975, 810; 530/388.9, 808, 809

[56] References Cited

U.S. PATENT DOCUMENTS 4,474,893  10/1984  Reading ................................. 436/547
4,722,899   2/1988  Hamaoka et al. ................... 435/172.2

OTHER PUBLICATIONS

Sevier et al., Clinical Chemistry, vol. 27, No. 11 pp. 1797–1806 (1981).
Clark et al., Hybridoma (3,1, p. 81) 1984.
Miller, Glenn A., et al., "Production of Monoclonal Antibodies to Salinomycin", Hybridoma, vol. 6, No. 4, 1986.
Beier, R. C., et al., "Enzyme Immunoassay for Detection of the Poultry Coccidiostat Salinomycin", Poultry Science, PSA and SPSS Abstracts, vol. 70, Supplement 1, 1991, Eightieth Annual Meeting of the Poultry Sci. Assoc., Aug. 12–16, 1991, Texas A&M Univ, College Station, Tex.

Primary Examiner—Christina Y. Chan
Attorney, Agent, or Firm—M. Howard Silverstein; Randall E. Deck; John D. Fado

[57] ABSTRACT

Hybridoma cell lines have been produced which produce and secrete monoclonal antibodies which bind salinomycin and are effective to detect salinomycin levels as low as about 0.174 to about 0.793 ng. These monoclonal antibodies may be used for the detection and quantitative determination of very low levels of salinomycin in samples, especially in animal tissue and feed material.

4 Claims, 3 Drawing Sheets

MONOCLONAL ANTIBODIES TO SALINOMYCIN AND METHOD FOR DETECTING THE SAME

BACKGROUND OF THE INVENTION

1. Field of the Invention

This invention relates to hybridoma cell lines and monoclonal antibodies produced therefrom which may be used to detect salinomycin, particularly in animal tissues and feeds.

2. Description of the Prior Art

The polyether ionophores are a major class of antimicrobials extensively used in agriculture as coccidiostats. Of these ionophoric anticoccidials, salinomycin has gained widespread acceptance, especially in the poultry industry, and has been marketed in all of the poultry producing countries of the world. In the United States, salinomycin is currently the most widely used anticoccidial in agriculture and the broiler industry.

Although salinomycin can be beneficial in broiler production when used properly, the agent is toxic and has a narrow margin of safety when given to chickens or other animals. Generally salinomycin is added to poultry feed as the free acid or its sodium salt at levels ranging fresh 44 to 66 ppm. When fed at higher than recommended levels, or when administered to sensitive animal species, salinomycin toxicosis can occur. For these reasons, an accurate, precise, and rapid method to analyze salinomycin is required.

Analysis of salinomycin in feeds or tissues has utilized bioassays (Official Methods of Analysis, 14th edition, AOAC, Arlington, Va., secs 1984, 42.266–42.270), thin-layer chromatography (Vanderkop and MacNeil, 1990, J. Chromatog., 508:386–390), and normal or reverse-phase HPLC using poet column derivatization with vanillin (Blanchflower et al., 1985, Analysy., 110:1283–1287; Martinez and Shimoda, 1986, J. Assoc. Off. Anal. Chem., 69:637–641; and LaPointe and Cohen, 1988, J. Assoc. Off. Anal. Chem. 71:480–484). However, most of these quantitative methods have significant disadvantages limiting their utility.

Immunoassay methods are rapidly gaining acceptance for the screening and quantification of a number of agricultural chemicals (Hammock and Mumma, In: Recent Advances in Pesticides: Analytical Methodology 1987, Harvey and Zweig Eds., ACS Symposium Series, American Chemical Society, Washington, D.C., 1980, pp. 321–352; Grierson et al., 1991, J. Agric. Food Chem, 39:2327–2331; and Shelby et al., 1992, J. Agric. Food Chem., 40:1090–1092). Miller et al. (1986, Hybridoma 5:353–360) produced monoclonal antibodies to salinomycin for use in an enzyme-linked immosorbent assay (ELISA). The immunogen used to produce the hybridoma cell lines was prepared by linkage of salinomycin to a carrier protein through a succinate moiety attached at the C-20 of the salinomycin molecule. The resultant monoclonal antibodies were reported sensitive to 50 ng of salinomycin per well.

SUMMARY OF THE INVENTION

We have now discovered hybridoma cell lines which produce and secrete monoclonal antibodies which bind salinomycin and are effective to detect salinomycin levels as low as about 0.174 to about 0.793 ng. We have unexpectedly found that the high affinity monoclonal antibodies of this invention may be obtained by using as an immunization agent or immunogen, salinomycin that has been coupled to an immunogenic carrier at the number one carbon of the salinomycin molecule (the carboxyl group). This highly effective immunization agent is preferably formed by first reacting salinomycin with N-hydroxysulfosuccinimide in the presence of N,N'-dicyclohexylcarbodiimide and under conditions effective to form salinomycin N-hydroxysulfosuccinimide ester. The resultant ester is then reacted with an immunogenic carrier under conditions effective to form an immunogenic salinomycin-carrier conjugate. The monoclonal antibody of this invention may be incorporated into kits for the detection and quantitative determination of low levels of salinomycin in samples, especially in animal tissue and feed material. Detection of salinomycin in sample materials is accomplished using immunosorbent assay procedures conventional in the art.

It is an object of this invention to provide hybridoma cell lines that produce and secrete high affinity monoclonal antibodies which selectively bind salinomycin, and which are effective for detecting salinomycin at very low levels.

Another object of this invention is to provide immunoassay methods for the measurement of salinomycin in animal tissue and feeds.

A further object is to provide kits useful for the assay of salinomycin which include the monoclonal antibodies described hereinabove.

Yet another object is to provide a method for recovering or removing salinomycin frown any material.

Other objects and advantages of this invention will become readily apparent from the ensuing description.

DETAILED DESCRIPTION OF THE INVENTION

Figure 1:
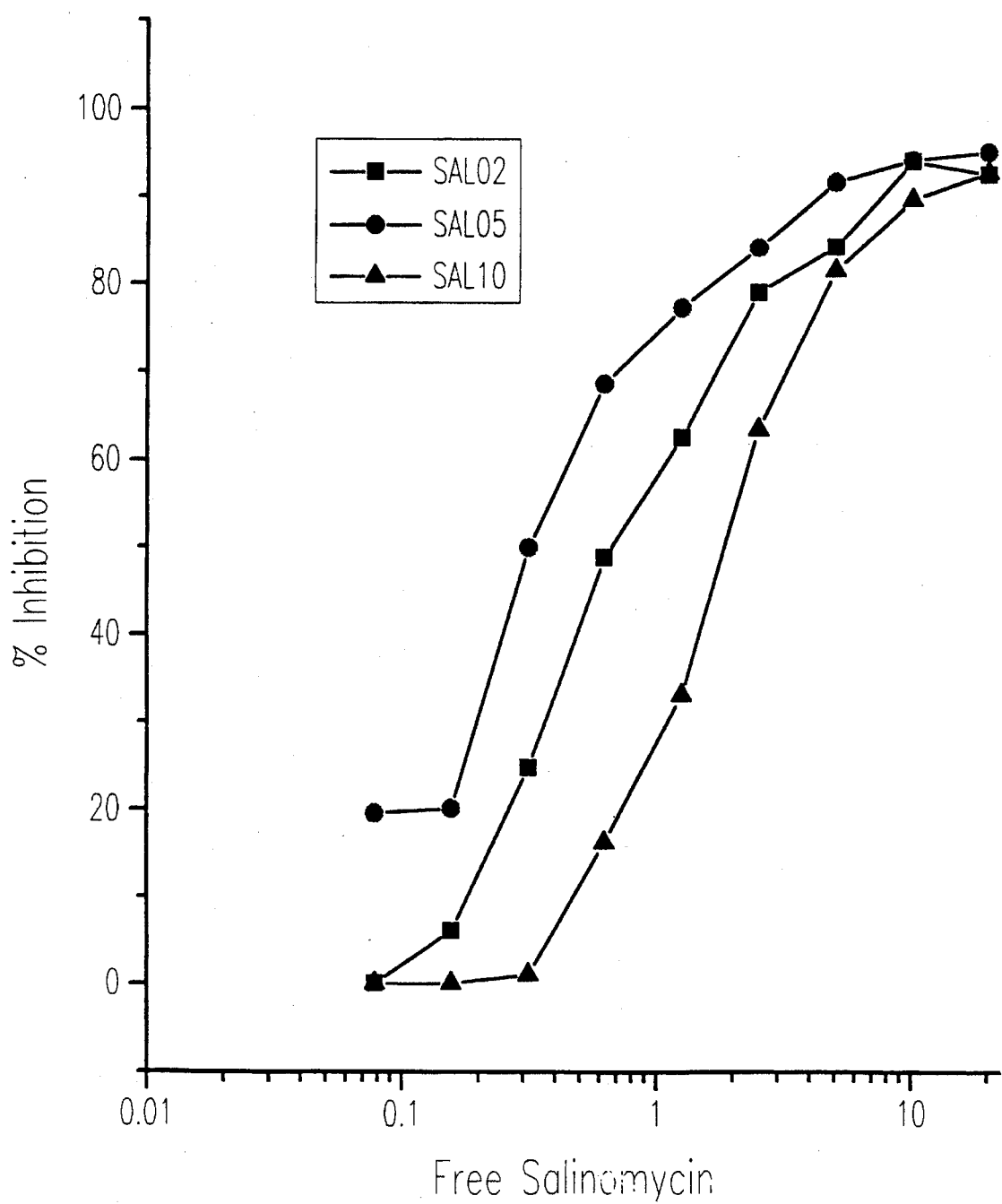
FIG. 1 shows competitive inhibition ELISA standard inhibition curves for three of the anti-salinomycin antibodies of the invention using free salinomycin as a competitor.

In accordance with this invention we have created hybridoma cell lines that produce monoclonal antibodies which bind salinomycin with high affinity and are effective for detecting and quantifying very low levels of the coccidiostat. The monoclonal antibodies of the invention possess significantly greater sensitivity than the antibodies of the prior art, and may detect salinomycin levels as low as about 0.174 to about 0.793 ng as determined by $IC_{20}$ in competitive inhibition ELISA.

Preparation of the hybridomas may be accomplished using conventional techniques such as described by Kohler and Milstein [Nature, 256:495–497 (1975)], Koprowski et al. [U.S. Pat. No. 4,196,265] or Wands [U.S. Pat. No. 4,271,145], the contents of each of which are incorporated by reference herein. Generally, the process of preparation comprises the steps of immunizing an animal with the antigen of interest, recovering splenocytes or lymphocytes from the animal, fusing the splenocytes or lymphocytes with continuously replicating myeloma cells to produce hybrid cells, and screening the resultant hybrid cells for the production of antibodies to the antigen. However, because salinomycin is a relatively small molecule, it is itself incapable of stimulating the immune system to produce antibodies. To render the compound immunogenic, it must first be conjugated to an immunogenic carrier in such a manner that the resultant immunogen is capable of stimulating the immune system of an animal to produce specific antibodies that are capable of binding the unconjugated salinomycin.

We have unexpectedly discovered that the immunogen resulting from coupling the carrier to salinomycin at its number one carbon by the process described hereinbelow, generates hybridoma cell lines which produce monoclonal antibodies of significantly greater sensitivity than previously attainable.

The method of preparing the hybridomas comprises the following steps:

Immunogen. The immunizing agent is constructed by covalently conjugating salinomycin to an immunogenic carrier at its number one carbon (the carboxyl group). Immunogenic carriers are defined herein as any compound to which salinomycin may be attached to render it immunogenic. Suitable carriers are well known and may be readily determined by the practitioner skilled in the art. Without being limited thereto, preferred carriers include proteins such as keyhole limpet hemocyanin (KLH), bovine serum albumin (BSA), ovalbumin and human thyroglobulin.

The method of conjugating the salinomycin to the carrier is critical, are involves a two step reaction. In the first step, salinomycin is reacted with N-hydroxysulfosuccinimide, in a suitable solvent and in the presence of N,N'-dicyclohexylcarbodiimide, under conditions effective to form salinomycin N-hydroxysulfosuccinimide ester of formula (I):

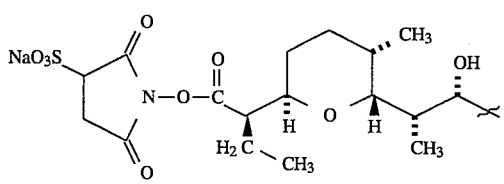

Dimethylformamide (DMF) is the preferred solvent although the skilled practitioner will recognize that other solvents may be readily determined. Alternative solvents include, but are not limited to, DMSO or dioxane. Applicants have discovered that alcoholic solvents such as methanol may destroy the salinomycin; Consequently, their use should be avoided. Reaction conditions (pH, temperature and time) are not critical and also may be readily determined by the skilled practitioner.

The resultant salinomycin N-hydroxysulfosuccinimide ester may then be reacted with the immunogenic carrier under conditions effective to form a salinomycin-carrier conjugate of formula (II):

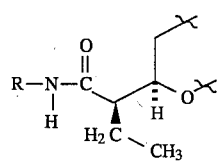

Again, reaction conditions are not critical and may be readily determined.

Immunization. To generate antibody-producing splenocytes or lymphocytes, an immunizing preparation comprising the salinomycin-carrier conjugate is injected into an immunologically competent animal. The preparation may also contain other proteins, although pure or substantially pure compositions of the conjugate in a pharmaceutically acceptable carrier are preferred.

Without being limited thereto, rate and particularly mice are preferred animals for immunization because of ease of handling. Preparation of hybridomas using splenocytes from these animals fused to a variety of myeloma cell lines have been reported by many investigators.

Inoculations of the animal can be by various routes. A series of three inoculations, generally at two week intervals, with a composition of the conjugate in isotonic saline with RIBI adjuvant elicits good antibody response, and is preferred. The skilled practitioner will recognize that other routes of administration, immunization schedules, and carriers or adjuvants may be used.

Hybridization. Splenocytes or lymphocytes recovered from the immunized animal are fused with continuously replicating tumor cells, such as myeloma or lymphoma cells, cultured, and hybridoma cells selected using techniques conventional in the art. Many continuously replicating tumor cell lines are available which may be used as fusion partners with the splenocytes. Without being limited thereto, preferred myeloma cells include P3, NS1, K653, and particularly SP2/0.

Fusion and culture of the cells can be performed using conventional techniques. In accordance with one well known effective procedure, the splenocytes and myeloma cells are fused by exposure to polyethylene glycol. Hybrid cells are selected by culture in hypoxanthine-aminopterin-thymidine (HAT) medium, whereby unfused myeloma cells are killed by HAT and splenocytes die out, leaving only the hybrid cells. The resultant hybridomas are then grown in HAT or other suitable culture medium and assayed for antibody production.

Screening. Samples of the supernatant culture fluid from the hybridomas are screened for antibodies to salinomycin. While the supernatants may be screened using a plurality of techniques such as RIA and ELISA, in accordance with the preferred embodiment, a modification of the direct-binding ELISA (db-ELISA) is employed. Generally, solid substrates, such as beads or the wells of a microtiter plate, which are coated with salinomycin or salinomycin-carrier conjugate, are used to bind anti-salinomycin antibody in the supernatants, and bound antibody is then detected. Detection of bound antibody may be accomplished by addition of enzyme-labeled anti-immunoglobulin antibodies followed by enzyme substrate. Horse radish peroxidase and its substrate, 2,2'-azinobis-3-ethylbenthiazolinesulfonic acid (ABTS) are preferred enzyme/substrate labels. However, it is understood that other enzyme/substrate labels or non-enzyme labels such as radiolabels or chromophores may also be used.

Cloning. Cloning of hybridomas which are positive for desired antibody production can be carried out as soon as they are detected by any method known in the art. Hybrid having a positive response in the ELISA screen are preferably expanded and subcloned one or more times by limiting dilution to assure monoclonality.

The supernatant culture fluid from the cloned hybridomas may also be screened to select for those producing antibodies having a high affinity for salinomycin. Affinity my be measured using a variety of well known techniques, such as ELISA, RIA or equilibrium dialysis using labelled salinomycin. Competitive inhibition ELISA is preferred, and is conducted at a final antibody concentration (dilution from tissue culture supernatant) to give 50% of maximal binding to a salinomycin coated substrate or assay well (i.e., the concentration of the antibody that resulted in 50% of the plateau activity in direct-binding ELISA). In accordance with this embodiment, the antibody containing supernatant is added to a salinomycin coated solid substrate such as the wells of an assay plate, together with a range of concentrations of free salinomycin as a competitor. Following incubation and washing, bound antibody in the wells is determined in the same manner as the db-ELISA. Percent inhibition may be calculated as $(1-B/B_O)\times 100$ where B is the OD of a well with a competitor and $B_O$ is the mean OD of the wells without competitor (control). The relative affinity of the antibodies may be accurately measured as the concentration of free salinomycin added to the wells that resulted in at least 20% inhibition ($IC_{20}$) of the control activity. However, for even greater accuracy, the affinity may be alternatively measured at 50% inhibition ($IC_{50}$).

Once hybridomas producing and secreting the desired anti-salinomycin antibodies are identified, large quantities of the antibody may be produced in tissue culture using well-known techniques. Alternatively, antibody may be produced within host animals, such as by ascites formation in syngeneic mice. Monoclonal antibodies so produced may be purified, for example, by affinity, chromatography on a protein A or G resin, or using salinomycin bound to a resin.

The monoclonal antibodies produced in accordance with this invention possess very high affinity for salinomycin, allowing the determination of the coccidiostat at very low levels. When the sensitivity of the antibodies is measured at $IC_{20}$, the detection limit for the antibodies varied from about 0.174 to about 0.793 ng of salinomycin (0.174–0.793 ng/well, using 100 µl samples added to micrititer plate wells) or 1.74 to 7.93 ppb. When measured at a higher standard of accuracy, i.e. $IC_{50}$, the detection limit for the antibodies varied from about 0.33 to 1.76 ng/well (100 µl sample/well) or 3.3 to 17.6 ppb. In contrast, as reported by Miller (ibid) the detection limit for previously developed antibodies to salinomycin was 50 ng.

The monoclonal antibodies of this invention may be used to detect and quantify salinomycin in unknown samples using well known immunosorbent assay procedures including but not limited to RIA or ELISA. A competitive inhibition ELISA similar to that used to screen the hybridomas is preferred. In this assay, a sample to be analyzed is incubated with the monoclonal antibody for salinomycin and a solid substrate coated with salinomycin. After incubation, the solid phase is drained, washed, bound antibody on the substrate is detected and percent inhibition calculated as described earlier. The concentration of salinomycin in the sample may then be determined by reference to a standard curve. A standard curve relating the percent inhibition (amount of bound antibody) to salinomycin concentration may be constructed from assays using known levels of salinomycin.

In one alternative embodiment, salinomycin may be determined by a competition ELISA such as described in Brandon et al. (U.S. Pat. No. 5,053,327, the contents of which are incorporated by reference herein) using the monoclonal antibody of the invention attached to a solid support. For example, the anti-salinomycin antibody may be immobilized on a bead or in a microtiter well. The unknown sample to be analyzed (or analytical standards of salinomycin) are then added with enzyme or radiolabeled salinomycin, and the amount of labeled salinomycin bound to the antibody is then measured, using a substrate when the label is an enzyme. The amount of salinomycin in the sample is inversely proportional to the amount of bound labeled salinomycin. In another alternative, the monoclonal antibody may be attached to a solid support for use in conventional double-antibody sandwich ELISA procedures.

With any of the above-described assay formats, the monoclonal antibodies of the invention may be incorporated into kits, alone or preferably together with any other necessary reagents. A preferred kit for use herein comprises a first container including the monoclonal antibody, a second container including detection means effective for detecting bound antibody, and a solid phase support having salinomycin attached thereto.

Determination of salinomycin in animal tissue samples or feeds may be conducted using the above-described assay with minimal sample preparation and without extensive extraction procedures. Samples need only be homogenized in buffer, such as Tris-HCl (pH 7.2), centrifuged, and the liquid phase recovered and used directly in the immunoassay. Although any animal tissue may be analyzed, the assay is particularly valuable for the determination of salinomycin in meats and liver. Tissue for analysis in accordance with the invention may originate from virtually any animal. Without being limited thereto, the analysis of tissue samples from domestic by this invention.

Another application of the monoclonal antibodies is affinity purification of salinomycin. The antibodies may be bound to a matrix, column, or other support using well-known techniques and used to recover or remove salinomycin from any desired material. Alternatively, the antibodies may be incorporated into sensors such as solid phase electronic devices for detection of salinomycin in sample materials.

The following examples are intended only to further illustrate the invention and are not intended to limit the scope of the invention which is defined by the claims.

EXAMPLE 1

Immunogen Preparation

Chemicals and Supplies. The following chemicals and supplies were purchased: Sodium salt of Salinomycin (Calbiochem, La Jolla, Calif.; #563080); Narasin (Elanco Products Co., Indianapolis, Ind.; #91059); Lasalocid (Aldrich Chemical Co., Milwaukee, Wiss.; #21,111–7); Monensin (Calbiochem, La Jolla, Calif.; #475896); HPTLC Pre-coated Plates (E. Merck, Germany; #5715); Omnisolv grade N,N-Dimethylformamide (DMF) and chloroform (E M Science, Gibbstown, N.J.); methanol (Fischer, Fair Lawn, N.J.); 1200–1400 mwco Dialysis Membrane Tubing (Scientific Products, McGaw Park, Ill.; #D1615-2); bovine serum albumin (BSA; #A-7030), keyhole limpet hemocyanin (KLH; #H-2133), DOWEX-50W cation exchange resin (#50x4–200), albumin (#A-5253), peroxidase-conjugated goat anti-mouse IgG (whole molecule) antiserum (#A5278), peroxidase substrate 2,2'-azinobis (3-ethylbenzothiazoline-6-sulfonic acid (ABTS; #A1888), hydrogen peroxide (#H1009) (Sigma Chemical Co., St. Louis Mo.); N-hydroxysulfosuccinimide (Sulfo-NHS, #2451) and N,N'-dicyclohexycarbodiimide (DCC, #20320)(Pierce Chemical Co., Rockford, Ill.), power supply and protein gel (TITAN 1500 and gel #3041, Helena Lab, Beaumont, Tex.); BALB/c mice (Harlan Sprague Dawley Inc., Indianapolis, Ind.), RIBI adjuvant (RIBI Immunochem Research Inc., Hamilton, Mo.); 96-well flat bottom microtiter plates (Falcon #3072, Becton Dickinson & Company, Lincoln Park, N.J.); food dehydrator (Excalibur, Sacramento, Calif.); isotype determination (SBA Clonotyping, Fisher, Pittsburgh, Pa.); tissue homogenizer (Tekmar, Cincinnati, Ohio).

Hapten Synthesis. Salinomycin-Na (0.66 mmol.) was dissolved in 3 mLs of DMF and eluted with DMF through a 10 cm HCl-equilibrated DOWEX-50W cation exchange column which had previously been washed with 2 volumes of 1 N HCl, 3 volumes of double distilled water, and 2 volumes of DMF. The Salinomycin (SAL) was eluted with DMF in 14.2 mL and divided into two fractions. Thin layer chromatography of the eluate was developed on concentration zone silica half-plates with chloroform:methanol (95:5). The SAL band had an Rf=0.97, which was equal to that of the acid form of SAL.

Salinomycin-KLH Conjugation: Sulfo-NHS, 0.117 mmol., dissolved in DMF (pH 8) was added to 2.4 mL of the SAL-DMF eluate. To SAL-Sulfo-NHS, 0.1183 mmol. of DCC in 1 mL of DMF (pH 8) was added and stirred at 23° C. for 12 hours. The SAL-sulfo-NHS mixture was added dropwise to KLH, 50 mg, in 10 ml of water (pH 8–9) and stirred at 23° C. overnight.

Salinomycin-BSA Conjugation: Sulfo-NHS, 0.59 mmol., dissolved in DMF (pH 8) was added to 11.8 mL of the SAL-DMF eluate. To SAL-sulfo-NHS, 0.5836 mmol. of DCC in 1 mL of DMF (ph 8), was added slowly and stirred at 23° C. for 12 hours. SAL-sulfo-NHS mixture was added dropwise to BSA, 250 mg, in 10 ml of water (pH 8–9) and stirred at 23° C. overnight.

Dialysis: Both SAL-KLH and SAL-BSA conjugates were dialized against DMF:water (80:20, pH 8–9) for 24-h. The concentration of DMF in the dialysis solution was decreased by 20% every 24-h until only water (pH 8) was present. The conjugates were separated into 0.5 mL aliquotes and frozen at −70° C. until used.

Electrophoresis: Both SAL-KLH and SAL-BSA conjugates were electrophoreased on agarose gel in comparison to KLH and BSA. The electrophoretic pattern indicated the presence of variable numbers of haptens bound to both protein molecules.

EXAMPLE 2

Hybridoma and Monoclonal Antibody Production

Hybridization. One-month-old BALB/c mice were injected intraperitoneally (ip) with 100 µg of SAL-KLH in 0.2 mL of isotonic saline with RIBI adjuvant. Mice received a single ip injection every other week for a total of three injections. Four days prior to fusion, the mouse was given an ip injection of 100 µg of SAL-KLH in 0.2 mL of saline with RIBI adjuvant. The spleen was removed and splenocytes were fused with SP2/0 myeloma cells and cultured under conditions described by Stanker et al. [J. Immunol., vol. 136, no. 11, pp. 4174–4180, (1986)] the contents of which are incorporated by reference herein. In review, SP2/0 myeloma cells were grown in a medium referred to as Dulbecco's modified Eagle's medium, which consists of Dulbecco's modified Eagle's medium (Life Technologies, Inc., Grand Island, N.Y.) with 35 mM NaHCO3, 2.9 mg/ml glutamine, penicillin G (20 units/ml), streptomycin sulfate (20 µg/ml) and 2%–4% fetal calf serum. The cells were maintained at 37° C. in closed vessels. Splenocytes were fused to SP2/0 myeloma cells using polyethylene glycol as described by Bigbee et al. [Mol. Immunol., vol. 20, page 1353 (1983)] the contents of which are incorporated by reference herein. The fused cells were then spread over 30 96-well microculture plates and were allowed to grow in the above media with the addition of HAT (hypoxanthine, 200 µM; aminopterin 0.8 µM; thymidine 32 µM) and 2% fetal calf serum at 37° C. was used for hybridoma cultures immediately after fusion; thereafter, HT (hypoxanthine) 100 µM; thymidine 16 µM) was added as needed through cloning by limited dilution in a humid, 5% $CO_2$ atmosphere for 10 to 14 days before screening for antibody-producing hybridomas. One or more growing hybridomas were observed in greater than 95% of the wells at 10 days. Abdominal macrophages from pristane-treated BALB/c mice were added to the medium ($2 \times 50^5$ cells/mL) to support hybridoma growth from fusion through cloning.

Screening. A modification of the direct-binding ELISA (db-ELISA), described by Stanker et al. [J. Agric. Food Chem., vol. 37, pp. 834–839, (1989), the contents of which are incorporated by reference] was used to screen tissue culture fluid from growing hybridomas for antibodies to SAL. The supernatant from each of the 2112-wells was screened. Briefly, 96-well flat bottom microtiter plates were coated with 100 µL of SAL-BSA (250 ng/well) in water and dried for 24-h at 37° C. in a food dehydrator. Nonreactive sites in each well on the microtiter plates were blocked for 1-h at 23° C. with 200 µL of 3% solution of albumin and incubated for 1-h at 37° C. with 100 µL of hybridoma supernatant containing the anti-SAL antibody. The plates were exhaustively washed with a solution of 0.05% TWEEN-20 in distilled water, and peroxidase-conjugated goat anti-mouse IgG (whole molecule) antiserum diluted 1/1000 in Tris-HCl assay buffer (ph 7.2) was added to each well. Following a second 1-h incubation at 37° C., the microtiter plates were exhaustively washed again with TWEEN-20/water and 100 µL of the peroxidase substrate (ABTS) with hydrogen peroxide in citrate buffer (pH 5.5) was added to each well. Absorbance measurements at 405 nm were taken after a 30-minute incubation at room temperature and the resulting data were analyzed.

Over 500 wells (approximately 25%) gave positive signals and were observed to have one or more hybridoma clones which were secreting antibodies that recognized some epitope on the SAL-BSA conjugate. The cells from those wells showing the strongest response (125 wells) were expanded and tested again in a competitive inhibition ELISA for their ability to recognize unconjugated (free) salinomycin.

For the competitive inhibition ELISA, the wells of a 96-well microtiter plate were coated with 250 ng SAL-BSA and blocked with ovalbumin as previously described. Two hundred µL of a competitor (free salinomycin at 20–100 ng/100 µL) in assay buffer, were added to row 2 of an antigen-coated well. The remaining wells in that row received 100 µL of assay buffer. A 100 µL aliquot of competitor was withdrawn from row 2 and serially diluted across the microtiter plate into wells 3–10. Wells 11 and 12 received no competitor. Next, 100 µL of a diluted monoclonal antibody that resulted in 50% of the plateau activity in a db-ELISA was added to each well of rows 2–12. Plates were incubated for 1-h at 37° C. and processed as described above in the db ELISA. Percent inhibition was calculated by the following method: $(1-B/B_0) \times 100$ where B=the OD of a well with a competitor and $B_0$=mean ODs of the wells without competitor (i.e. wells 11 and 12).

Forty of the hybridomas produced antibodies that recognized unconjugated salinomycin. The most active of these hybrid were subcloned twice by limiting dilution to guarantee their monoclonal origin. This resulted in 16 clones. The monoclonal antibodies produced by these 16 clones were named SAL02-SAL13 and SAL22-SAL25. The competitive inhibition ELISA results for three of the 16 monoclonal antibodies (ranging from the most to least sensitive) are shown in FIG. 1. The concentrations of salinomycin that resulted in 20% inhibition ($IC_{20}$) of control activity (i.e.

wells 11 and 12 with no competitor present) ranged from 0.174 ng (SAL05) to 0.793 ng (SAL10). The concentrations that resulted in 50% inhibition $IC_{50}$ for these same antibodies ranged from 0.33 to 1.76 ng, respectively.

The above-mentioned hybridoma cell line which produces and secretes monoclonal antibody SAL02 has been deposited under the Budapest Treaty in the American Type Culture Collection (12301 Parklawn Drive, Rockville, Md., 20852, USA) on Jul. 6, 1995, and has been assigned Deposit No. ATCC HB 11954.

Isotype Determination. Isotype determinations were conducted for all 16 antibodies by isotype specific ELISA using heavy- and light-chain-specific antiserum. All antibodies were determined to be IgG2a antibodies with kappa light chains.

Figure 2:
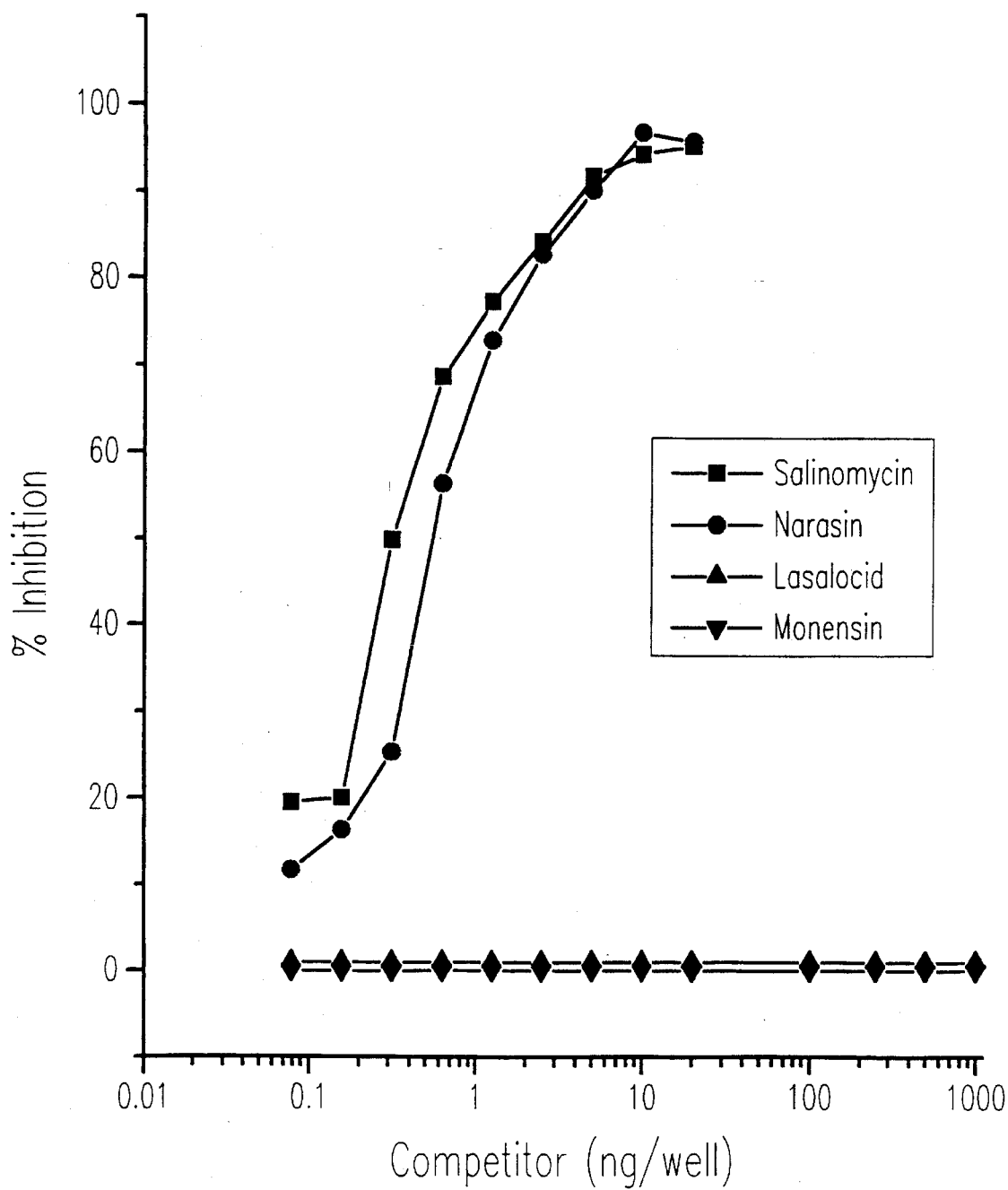
FIG. 2 shows competitive inhibition ELISA inhibition curves for monoclonal antibody SAL05 with the ionophores salinomycin, narasin, lasalocid and monensin as competitors.

Antibody Characterization. The 16 monoclonal antibodies were further evaluated for their ability to distinguish between commonly used ionophoric coccidiostats. The competitive inhibition ELISA described supra was repeated with the ionophores salinomycin (SAL), narasin (NAR), lasalocid (LAS) and monensin (MON) as competitors. The $IC_{50}$ for 13 of the 16 monoclonal antibodies were not significantly different in their abilities to distinguish between salinomycin and narasin as summarized in Table 1. None of the 16 antibodies recognized lasalocid or monensin at or below 1000 ng/well (no inhibition of antigen-antibody binding). Representative inhibition curves for the monoclonal antibody SAL05 are shown in FIG. 2.

EXAMPLE 3

Salinomycin Assay

Extraction of Salinomycin From Liver. Liver was taken from 16, twenty-one day old male broiler chicks (Hubbard× Hubbard) which had been fed ad libitum with feed containing no coccidiostats. One gram sample from each liver was spiked with 1000, 500, 250, 125, or 62.5 ng of SAL and stored for 24-h at 4° C. Following storage, 10 mL of ice cold assay buffer was added to each spiked liver sample and homogenized for 1 min. The homogenate was centrifuged at 1000 g for 10 min. at 4° C. The liquid phase was recovered for analysis.

Figure 3:
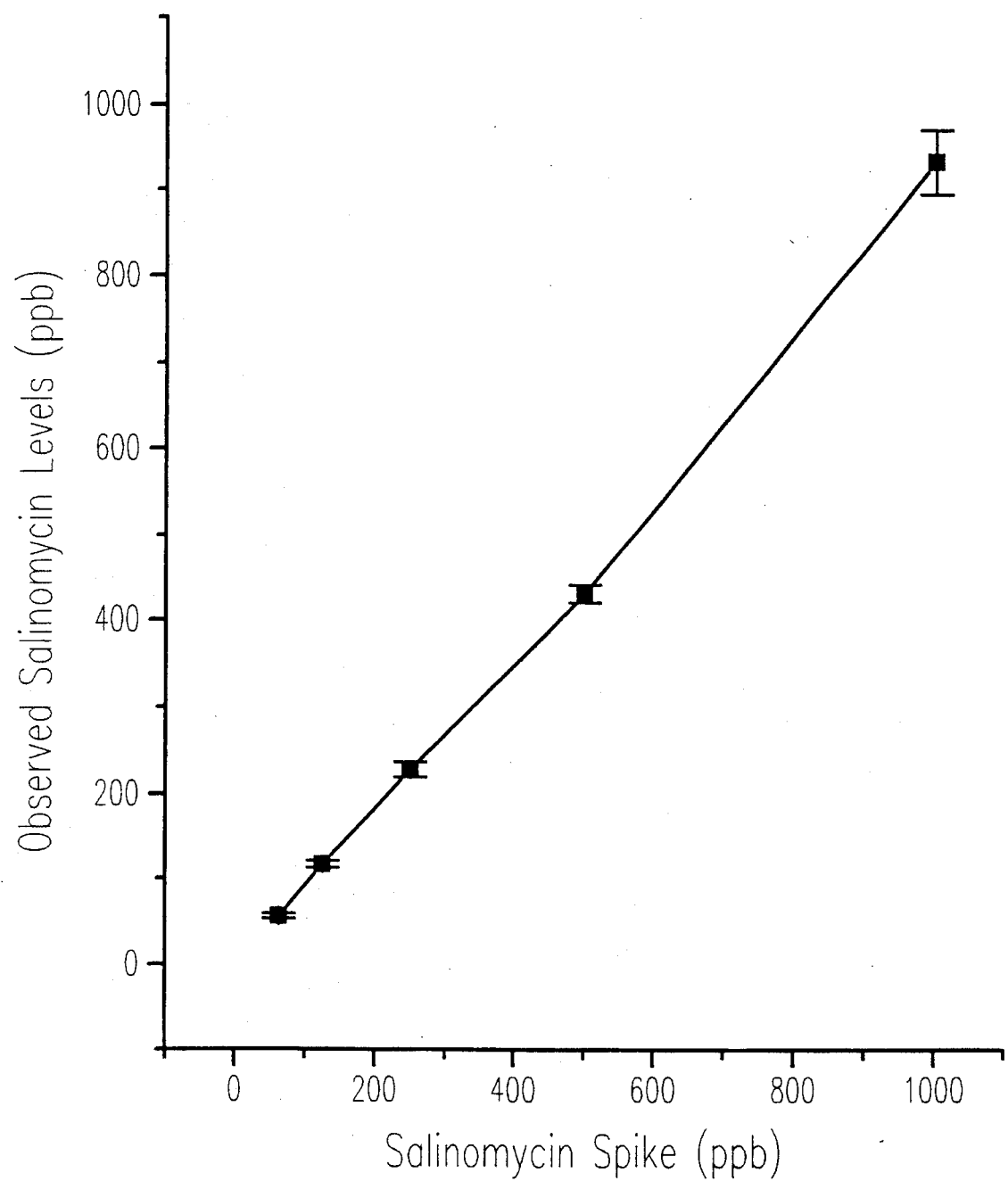
FIG. 3 shows the results of a competitive inhibition ELISA using the antibody SAL05 to measure salinomycin in spiked liver samples.

Immunoassay. The liquid phase from the liver samples was analyzed for salinomycin content using the competitive inhibition ELISA described supra, with SAL05 as the antibody. The percent inhibition for each sample was measured and the values compared to a standard curve similar to FIG. 1 to determine salinomycin concentration. Liver samples spiked with 62.5, 125, 250, 500 and 1000 ppb SAL were determined to have 55.8, 117, 229, 431 and 934 ppb of SAL, respectively (FIG. 3). The correlation between the spike and observed levels was 0.9990. The means for the observed levels were 91±3% of the spiked levels.

It is understood that the foregoing detailed description is given merely by way of illustration and that modifications and variations may be made therein without departing from the spirit and scope of the invention.

TABLE I

Mean 50% Inhibition Values ($IC_{50}$) of Competitors for the Sixteen Anti-Salinomycin Monoclonal Antibodies

| Antibodies | Competitors (ng/well) | |
|---|---|---|
| | SAL[1] | NAR[2] |
| SAL02 | 0.62 ± 0.11[3] | 0.97 ± 0.97[3] |
| SAL03 | 0.78 ± 0.72 | 0.82 ± 0.58 |
| SAL04 | 0.35 ± 0.17 | 0.34 ± 0.15 |
| SAL05 | 0.33 ± 0.10[b] | 0.52 ± 0.62[a] |
| SAL06 | 0.78 ± 0.62 | 0.39 ± 0.15 |
| SAL07 | 1.44 ± 1.28 | 0.93 ± 0.85 |
| SAL08 | 0.60 ± 0.30[b] | 1.09 ± 0.15[a] |
| SAL09 | 0.97 ± 0.28 | 1.17 ± 0.27 |
| SAL10 | 1.76 ± 0.29[a] | 1.18 ± 0.49[b] |
| SAL11 | 0.57 ± 0.25 | 0.69 ± 0.28 |
| SAL12 | 0.49 ± 0.28 | 0.67 ± 0.19 |
| SAL13 | 0.75 ± 0.49 | 0.55 ± 0.20 |
| SAL22 | 0.56 ± 0.23 | 0.51 ± 0.09 |
| SAL23 | 0.92 ± 0.15 | 0.99 ± 0.25 |
| SAL24 | 1.15 ± 0.45 | 0.98 ± 0.46 |
| SAL25 | 0.61 ± 0.18 | 0.68 ± 0.34 |

SAL[1] = Salinomycin, NAR[2] = Narasin, Mean ± SD[3], n = 10
For each monoclonal antibody, means with different superscripts are significantly different from each other at p > 0.05 (i.e. SAL05, SAL08, and SAL10).

Neither Lasalocid or Monensin inhibited the antigen-antibody binding at or below 100 ng/well (10 ppm).
The means are based upon 10 independent assays run on 10 different days during a two week period.

We claim:

1. A hybridoma cell line ATCC HB 11954 which produces and secretes monoclonal antibody SAL02 which specifically binds to salinomycin, and wherein said hybridoma cell line is produced using an immunization preparation comprising salinomycin conjugated at its number 1 carbon to an immunogenic carrier.

2. The hybridoma cell line of claim 1 which is produced using an immunization preparation comprising salinomycin conjugated to an immunogenic carrier, said preparation formed by the process comprising:

(a) reacting N-hydroxysulfosuccinimide with salinomycin in the presence of N,N'-dicyclohexylcarbodiimide under conditions effective to form salinomycin N-hydroxysulfosuccinimide ester; and (b) reacting said ester with an immunogenic carrier under conditions effective to form an immunogenic salinomycin-carrier conjugate.

3. A monoclonal antibody produced by the hybridoma cell line of claim 1.

4. A kit for detecting salinomycin in animal tissue or feed material comprising the monoclonal antibody produced by the hybridoma cell line of claim 1.

* * * * *